United States Patent
Rosenberg

(10) Patent No.: US 10,046,142 B2
(45) Date of Patent: *Aug. 14, 2018

(54) ANCHOR INSTRUMENTATION AND METHODS

(71) Applicant: INTERRAD Medical, Inc., Plymouth, MN (US)

(72) Inventor: Michael S. Rosenberg, Eagan, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 843 days.

This patent is subject to a terminal disclaimer.

(21) Appl. No.: 14/548,766

(22) Filed: Nov. 20, 2014

(65) Prior Publication Data

US 2015/0080804 A1 Mar. 19, 2015

Related U.S. Application Data

(60) Continuation of application No. 13/405,501, filed on Feb. 27, 2012, now Pat. No. 8,920,380, which is a continuation of application No. 12/793,261, filed on Jun. 3, 2010, now Pat. No. 8,142,401, which is a division of application No. 11/763,576, filed on Jun. 15, 2007, now Pat. No. 7,753,889.

(51) Int. Cl.
*A61M 25/04* (2006.01)
*A61M 25/06* (2006.01)
*A61M 25/02* (2006.01)

(52) U.S. Cl.
CPC ........ *A61M 25/04* (2013.01); *A61M 25/0662* (2013.01); *A61M 2025/0213* (2013.01)

(58) Field of Classification Search
None
See application file for complete search history.

(56) References Cited

U.S. PATENT DOCUMENTS

| | | |
|---|---|---|
| 2,525,398 A | 10/1950 | Collins |
| 3,059,645 A | 10/1962 | Hasbrouck et al. |
| 3,108,595 A | 10/1963 | Overment |
| 3,176,690 A | 4/1965 | H''Doubler |
| 3,630,195 A | 12/1971 | Santomieri |

(Continued)

FOREIGN PATENT DOCUMENTS

| | | |
|---|---|---|
| FR | 2 625 897 | 7/1989 |
| WO | WO 1991/015254 | 3/1991 |

(Continued)

OTHER PUBLICATIONS

U.S. Appl. No. 60/412,453, filed Sep. 20, 2002, Claude.

(Continued)

*Primary Examiner* — Nathan R Price
*Assistant Examiner* — Weng Lee
(74) *Attorney, Agent, or Firm* — Fish & Richardson P.C.

(57) ABSTRACT

Some embodiments of a medical device anchor system includes an anchor sleeve and a catheter (or other medical instrument) to advance through a working channel of the anchor sleeve. The anchor sleeve may have a subcutaneous cuff device arranged along an outer surface. In such circumstances, the embedded cuff device can inhibit the migration of infection from outside the skin and into the blood stream.

19 Claims, 13 Drawing Sheets

(56) References Cited

U.S. PATENT DOCUMENTS

| | | |
|---|---|---|
| 3,677,250 A | 7/1972 | Thomas |
| 3,717,151 A | 2/1973 | Collett |
| 3,834,380 A | 9/1974 | Boyd |
| 3,856,009 A | 12/1974 | Winnie |
| 3,896,527 A | 7/1975 | Miller et al. |
| 3,938,529 A | 2/1976 | Gibbons |
| 4,043,346 A | 8/1977 | Mobley et al. |
| 4,114,618 A | 9/1978 | Vargas |
| 4,248,224 A | 2/1981 | Jones |
| 4,309,994 A | 1/1982 | Grunwald |
| 4,397,647 A | 8/1983 | Gordon |
| 4,474,569 A | 10/1984 | Newkirk |
| 4,592,356 A | 6/1986 | Gutierrez |
| 4,645,492 A | 2/1987 | Weeks |
| 4,665,906 A | 5/1987 | Jervis |
| 4,799,495 A | 1/1989 | Hawkins et al. |
| 4,804,359 A | 2/1989 | Grunwald et al. |
| 4,813,930 A | 3/1989 | Elliot |
| 4,936,823 A | 6/1990 | Colvin et al. |
| 4,986,810 A | 1/1991 | Semrad |
| 5,041,085 A | 8/1991 | Osborne et al. |
| 5,067,957 A | 11/1991 | Jervis |
| 5,122,122 A | 6/1992 | Allgood |
| 5,190,546 A | 3/1993 | Jervis |
| 5,209,723 A | 5/1993 | Twardowski et al. |
| 5,256,146 A | 10/1993 | Ensminger et al. |
| 5,263,939 A * | 11/1993 | Wortrich ............ A61B 17/34 128/DIG. 26 |
| 5,312,337 A | 5/1994 | Flaherty et al. |
| 5,344,439 A | 9/1994 | Otten |
| 5,378,239 A | 1/1995 | Termin et al. |
| 5,456,671 A | 10/1995 | Bierman |
| 5,496,277 A | 3/1996 | Termin et al. |
| 5,509,897 A | 4/1996 | Twardowski et al. |
| 5,578,013 A | 11/1996 | Bierman |
| 5,597,378 A | 1/1997 | Jervis |
| 5,599,311 A | 2/1997 | Raulerson |
| 5,681,288 A | 10/1997 | Schlitt |
| 5,688,247 A | 11/1997 | Haindl et al. |
| 5,702,371 A | 12/1997 | Bierman |
| 5,722,959 A | 3/1998 | Bierman |
| 5,728,133 A | 3/1998 | Kontos |
| 5,741,234 A | 4/1998 | Aboul-Hosn |
| 5,746,720 A | 5/1998 | Stouder, Jr. |
| 5,749,835 A | 5/1998 | Glantz |
| 5,755,697 A | 5/1998 | Jones et al. |
| 5,769,821 A | 6/1998 | Abrahamson et al. |
| 5,800,402 A | 9/1998 | Bierman |
| 5,810,781 A | 9/1998 | Bierman |
| 5,827,230 A | 10/1998 | Bierman |
| 5,833,667 A | 11/1998 | Bierman |
| 5,857,999 A | 1/1999 | Quick et al. |
| 5,921,965 A | 7/1999 | Blei |
| 5,928,266 A | 7/1999 | Kontos |
| 5,944,732 A | 8/1999 | Raulerson et al. |
| 5,947,931 A | 9/1999 | Bierman |
| 5,971,960 A | 10/1999 | Flom et al. |
| 5,989,213 A | 11/1999 | Maginot |
| 5,989,265 A | 11/1999 | Bouquet De La Joliniere et al. |
| 6,071,263 A | 6/2000 | Kirkman |
| 6,112,111 A | 8/2000 | Glantz |
| 6,126,631 A | 10/2000 | Loggie |
| 6,190,371 B1 | 2/2001 | Maginot et al. |
| 6,213,979 B1 | 4/2001 | Bierman |
| 6,290,676 B1 | 9/2001 | Bierman |
| 6,293,927 B1 | 9/2001 | McGuckin, Jr. |
| 6,413,240 B1 | 7/2002 | Bierman et al. |
| 6,447,485 B2 | 9/2002 | Bierman |
| 6,471,689 B1 | 10/2002 | Joseph |
| 6,475,207 B1 | 11/2002 | Maginot |
| 6,540,693 B2 | 4/2003 | Burbank et al. |
| 6,572,588 B1 | 6/2003 | Bierman et al. |
| 6,582,403 B1 | 6/2003 | Bierman et al. |
| 6,638,242 B2 | 10/2003 | Wilson et al. |
| 6,663,600 B2 | 12/2003 | Bierman et al. |
| 6,679,851 B2 | 1/2004 | Burbank et al. |
| 6,695,861 B1 | 2/2004 | Rosenberg et al. |
| 6,743,218 B2 | 6/2004 | Maginot et al. |
| 6,770,055 B2 | 8/2004 | Bierman et al. |
| 6,796,976 B1 | 9/2004 | Chin et al. |
| 6,872,198 B1 | 3/2005 | Wilson et al. |
| 6,896,665 B2 | 5/2005 | Picha et al. |
| 6,958,044 B2 | 10/2005 | Burbank et al. |
| 7,008,412 B2 | 3/2006 | Maginot |
| 7,056,286 B2 | 6/2006 | Ravenscroft et al. |
| 7,753,889 B2 | 7/2010 | Rosenberg |
| 8,142,401 B2 | 3/2012 | Rosenberg |
| 8,920,380 B2 | 12/2014 | Rosenberg |
| 2002/0068898 A1 | 6/2002 | McGuckin et al. |
| 2002/0068899 A1 | 6/2002 | McGuckin, Jr. et al. |
| 2002/0107506 A1 | 8/2002 | McGuckin, Jr. et al. |
| 2002/0165489 A1 | 11/2002 | McGuckin et al. |
| 2003/0088213 A1 | 5/2003 | Schweikert et al. |
| 2003/0144657 A1 | 7/2003 | Bowe et al. |
| 2003/0195525 A1 | 10/2003 | Peterson et al. |
| 2005/0187578 A1* | 8/2005 | Rosenberg ............ A61M 25/04 606/232 |
| 2006/0129134 A1* | 6/2006 | Kerr ................ A61M 25/0097 604/539 |
| 2007/0078397 A1 | 4/2007 | Weststrate |
| 2007/0106330 A1 | 5/2007 | Rosenberg |
| 2007/0225651 A1 | 9/2007 | Rosenberg et al. |
| 2008/0275401 A1 | 11/2008 | Sage et al. |
| 2015/0080804 A1 | 3/2015 | Rosenberg |

FOREIGN PATENT DOCUMENTS

| | | |
|---|---|---|
| WO | WO 2004/026152 | 4/2004 |
| WO | WO 2005/039419 | 5/2005 |
| WO | WO 2005/102438 | 11/2005 |

OTHER PUBLICATIONS

Johnson & Johnson web page printout, "The EndoANCHOR Comparative Summary," printed Sep. 13, 2005.
Johnson & Johnson web page printout, "The EndoANCHOR Features and Benefits," printed Sep. 13, 2005.
Johnson & Johnson web page printout, "The EndoANCHOR Firing Sequence," printed Sep. 13, 2005.
Web Page printout of Statlock Device, author and date unknown.
European Search Report for EP 08158277.7, dated Sep. 11, 2008, 9 pages.

* cited by examiner

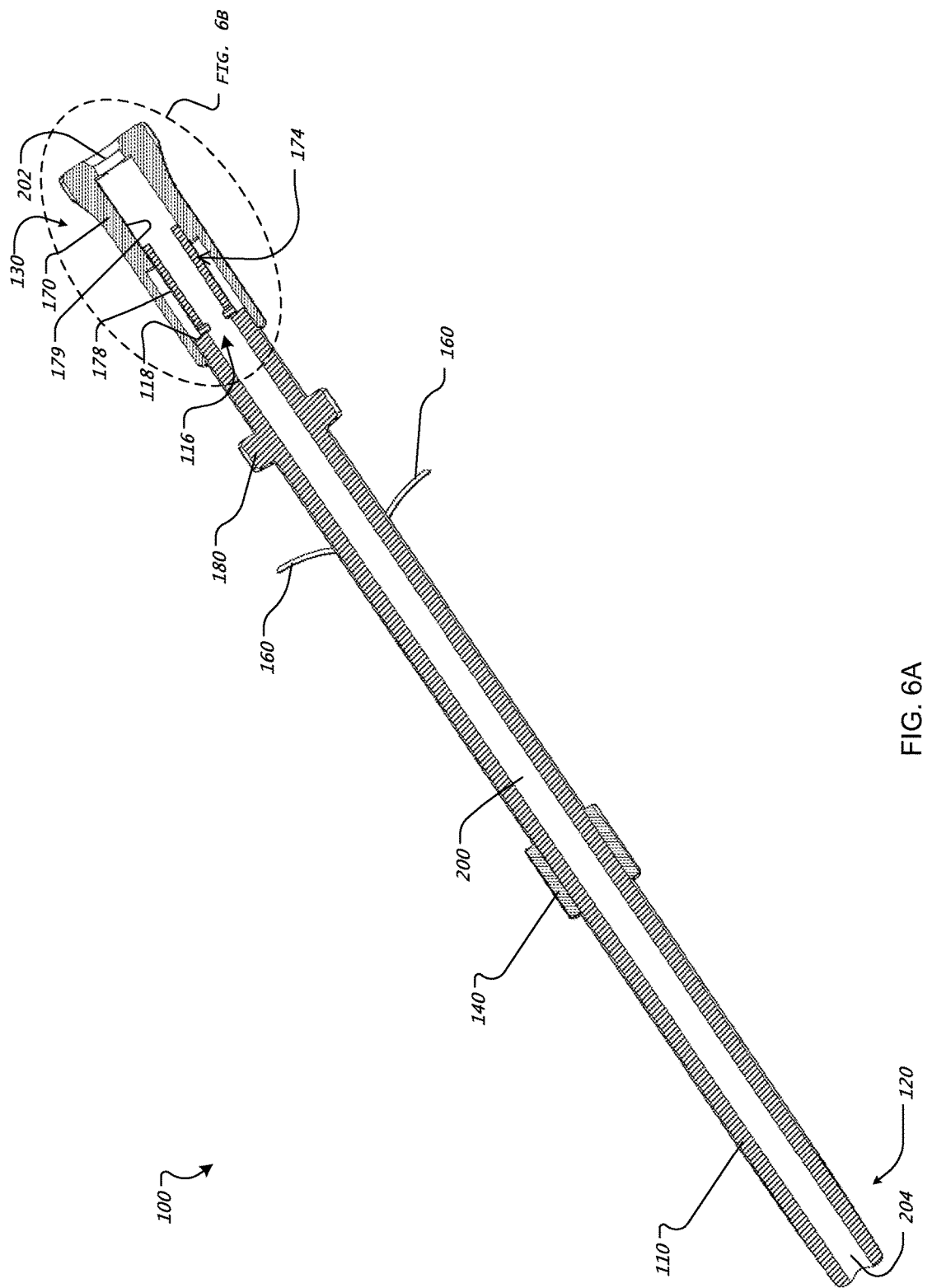

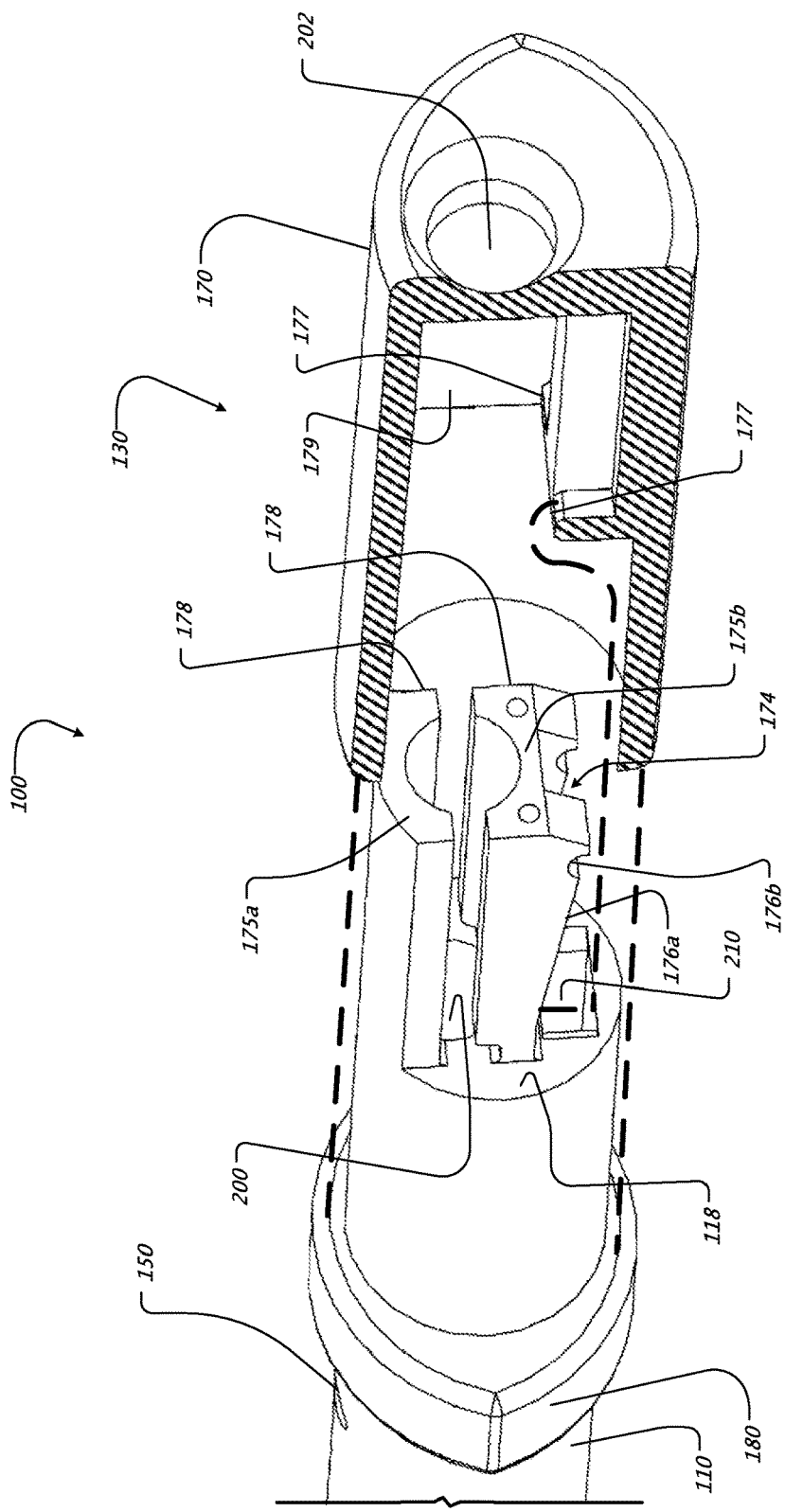

ANCHOR INSTRUMENTATION AND METHODS

CROSS-REFERENCE TO RELATED APPLICATION(S)

This application is a continuation of U.S. patent application Ser. No. 13/405,501 filed on Feb. 27, 2012 by Michael S. Rosenberg, which is a continuation of U.S. patent application Ser. No. 12/793,261 filed on Jun. 3, 2010 by Michael S. Rosenberg, which is a division of U.S. patent application Ser. No. 11/763,576 filed on Jun. 15, 2007 by Michael S. Rosenberg, the contents of which are incorporated herein by reference.

TECHNICAL FIELD

This document relates to anchor instrumentation, such as an anchor device for use in placement of a catheter or other medical instrument.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Following introduction into the patient, the catheter is typically secured to the patient using a tape patch or by suturing an attached hub to the skin. Some catheters may be delivered to a particular site in the body and remain in position for an extended period of time. For example, chronic dialysis patients may have a dialysis catheter arranged in a blood vessel for weeks or months at a time.

SUMMARY

Some embodiments of a medical device anchor system include an anchor sleeve and a catheter (or other medical instrument) to advance though a working channel of the anchor sleeve. The anchor sleeve may have a subcutaneous cuff device arranged along an outer surface. The subcutaneous cuff device can receive ingrowth of bodily tissue over a period of time when disposed in the subcutaneous layer. In such circumstances, the embedded cuff device can inhibit the migration of infection from outside the skin, along the anchor system, and into the blood stream. Furthermore, in the embodiments in which the cuff device is arranged on the anchor sleeve (rather than on the catheter body), the catheter can be distally advanced such that the cuff-to-tip distance from the subcutaneous cuff device to the catheter tip can be selectively adjusted. Thus, the cuff-to-tip distance can be customized by a practitioner while the catheter tip is inside the patient's body depending on the size of the patient, the anatomy of the patient, and other factors.

In some embodiments, an anchor sleeve device may include an elongate body that defines at least one working channel extending from a proximal portion to a distal tip portion. The anchor sleeve device may also include a subcutaneous anchor mechanism coupled to the elongate body. The subcutaneous anchor mechanism may have one or more flexible anchors that extend away from the body wall when in a deployed orientation in a subcutaneous layer. The anchor sleeve device may further include a subcutaneous cuff device arranged along an outer surface of the elongate body at a position distally of the one or more flexible anchors. The subcutaneous cuff device may comprise a biocompatible material to receive ingrowth of bodily tissue when disposed in the subcutaneous layer.

Particular embodiments may include an anchor system for placement of a catheter device. The anchor system may include an anchor sleeve having an elongate body that defines at least one working channel extending from a proximal portion to a distal tip portion of the anchor sleeve. The anchor sleeve may also have a subcutaneous cuff device arranged along an outer surface of the elongate body. The subcutaneous cuff device may comprise a biocompatible material to embed in bodily tissue when disposed in a subcutaneous layer. The anchor system may also include a catheter device to advance though the working channel of the anchor sleeve and into a targeted body site. The catheter device may define at least one lumen that extends to a catheter tip opening. When the catheter device is advanced through the working channel of the anchor sleeve, a distance from the subcutaneous cuff device to the catheter tip opening can be adjusted.

Some embodiments include a method of delivering a catheter device to an internal body site. The method may include advancing an anchor sleeve through a percutaneous opening so that a subcutaneous cuff device arranged along an outer surface of the anchor sleeve is disposed in a subcutaneous region. The subcutaneous cuff device may comprise a biocompatible material that receives tissue ingrowth when disposed in the subcutaneous region. The method may also include advancing a catheter device though a working channel of the anchor sleeve and toward a targeted body site. The catheter device may define at least one lumen that extends to a catheter tip. The distance from the subcutaneous cuff device to the catheter tip may define a cuff-to-tip distance. The method may further include adjusting the cuff-to-tip distance by moving the catheter device relative to the anchor sleeve while the subcutaneous cuff device is disposed in the subcutaneous region.

In certain embodiments, an anchor sleeve device includes an elongate body that defines at least one working channel extending from a proximal opening to a distal tip opening so as to receive a catheter. The anchor sleeve device may also include a subcutaneous anchor mechanism coupled to the elongate body. The subcutaneous anchor mechanism may have one or more flexible anchors that extend away from the body wall when in a deployed orientation in a subcutaneous layer. The anchor sleeve device may further include a locking device that releasably affixes to the catheter when the catheter is received in the working channel. The anchor sleeve device may also include an actuator that is adjustable relative to the elongate body from a first position to a second position. The adjustment of the actuator may simultaneously shift the flexible anchors to the deployed orientation and shift the locking device to compress at least a portion of an outer surface of the catheter when the catheter is received in the working channel.

These and other embodiments may provide one or more of the following advantages. First, the subcutaneous cuff device arranged along an outer surface of the anchor sleeve can serve as a barrier to infection. For example, the subcutaneous cuff device can receive ingrowth of bodily tissue or otherwise embedded into the surrounding tissue over a period of time, thereby inhibiting the migration of infection from outside the skin and into the blood stream.

Second, in some embodiments, a catheter or other medical instrument can be distally advanced such that the cuff-to-tip distance from the subcutaneous cuff device to the instrument tip can be selectively adjusted. Thus, the cuff-to-tip distance can be customized by a practitioner while the catheter tip is inside the patient's body depending on the size of the patient, the anatomy of the patient, and other factors.

Third, because the cuff-to-tip distance can be selectively adjusted by the practitioner during use in a patient, there is a reduced need to maintain an inventory of catheters having a fixed cuff-to-tip distance. For example, some catheters included a cuff device affixed on an outer surface of the catheter body, thereby providing a fixed and nonadjustable cuff-to-tip distance. Hospitals or clinics would maintain a vast inventory of these catheter-cuff devices so that a wide variety of cuff-to-tip distances can be selected and used by the practitioners. In some embodiments described herein, the cuff device is arranged on an anchor sleeve that is movable relative to the catheter, thereby providing an adjustable cuff-to-tip distance. As such, hospitals or clinics may no longer be required to maintain vast inventories of catheters having a range of fixed cuff-to-tip distances.

Fourth, some embodiments of the anchor sleeve may include subcutaneous anchors that retain the anchor sleeve in the subcutaneous region. For example, the anchors may comprise adjustable tines comprising a material that exhibits superelasticity when used in a human body (e.g., Nitinol or the like). The anchors can be deployed in the subcutaneous region so as to at least temporarily retain the anchor sleeve in engagement with the patient's body while the cuff device embeds with the surrounding tissue over a period of time. Thereafter, the cuff device may function as a long term anchor instrument in place of, or in addition to, the previously described tines.

Fifth, some embodiments of the anchor sleeve may include a locking device that can be actuated to releasably secure the catheter (or other medical instrument) to the sleeve body after the catheter has been advanced through the sleeve device toward a targeted location. In some circumstances, the locking device can also form a seal around the catheter when connected thereto. A single actuator can be adjusted to contemporaneously shift the flexible anchors to a deployed orientation in the subcutaneous region and shift the locking device to act upon the catheter.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6A is another cross-sectional view of the anchor sleeve device of FIG. 3.

FIG. 6B is an exploded perspective view of an actuator of the anchor sleeve of FIG. 6A.

Like reference symbols in the various drawings indicate like elements.

DETAILED DESCRIPTION OF ILLUSTRATIVE EMBODIMENTS

Some embodiments of a medical device anchor system include an anchor sleeve and a catheter (or other medical instrument) to advance though a working channel of the anchor sleeve. As described in more detail below, the anchor sleeve may have a subcutaneous cuff device that embeds with the surrounding bodily tissue when disposed in the subcutaneous layer over a period of time. In such circumstances, the embedded cuff device can inhibit the migration of infection from outside the skin, along the anchor system, and into the blood stream. Also as described in more detail below, the catheter is movable relative to the anchor sleeve, so the cuff-to-tip distance can be selectively adjusted by a practitioner while the catheter tip is inside the patient's body.

Figure 1:
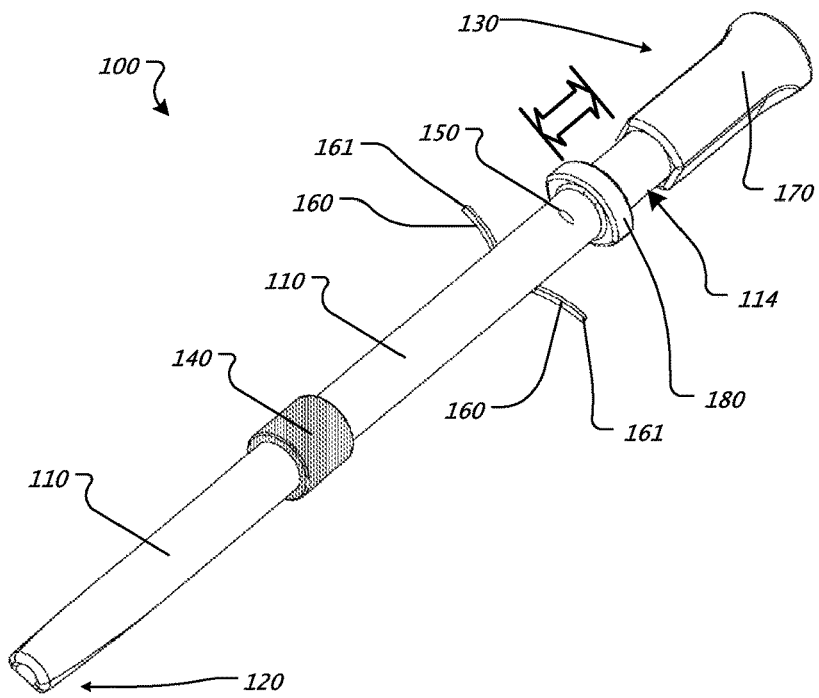
FIG. 1 is a perspective view of an anchor sleeve device in accordance with some embodiments.
Figure 2:
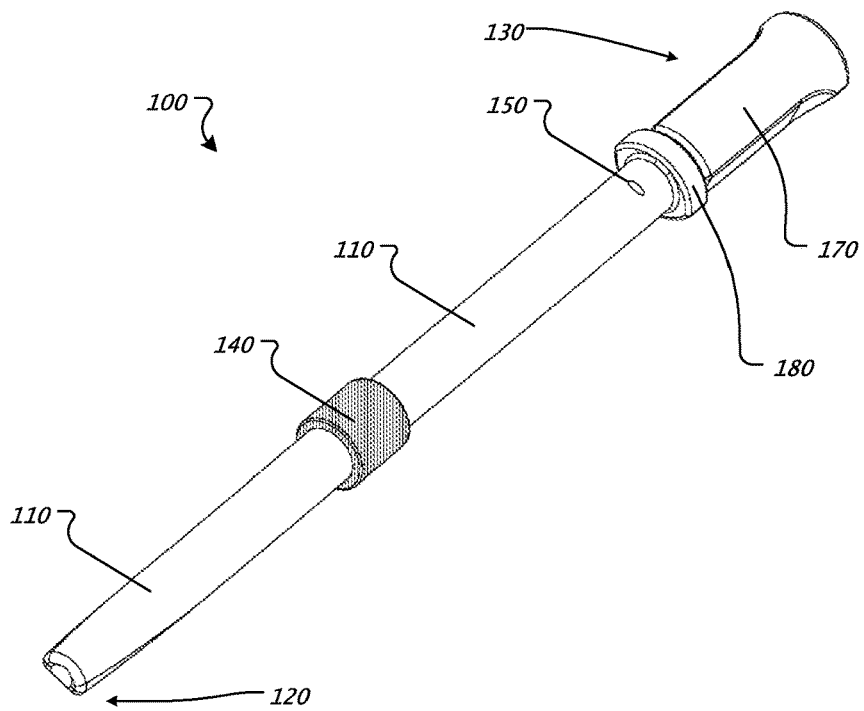
FIG. 2 is a perspective view of the anchor sleeve device of FIG. 1 with the anchors is a non-deployed position.

Referring to FIGS. 1-2, an anchor sleeve device 100 can be used in a system for placement of a catheter or other medical instrument into the body of a patient. The sleeve device 100 may include an elongate body 110, into which a catheter or other medical instrument can be inserted. The sleeve device 100 includes a distal tip portion 120 that may penetrate through a skin entry point and into the subcutaneous layer adjacent to the skin. Also, the sleeve device 100 includes a proximal portion 130 that can remain external to the skin so as to provide an insertion path for a catheter or other medical instrument. As described in more detail below, some embodiments of the sleeve device 100 may include a cuff 140, a depth indicator 150, one or more subcutaneous anchors 160, an actuator 170, a stopper 180, or a combination thereof.

Figure 7:
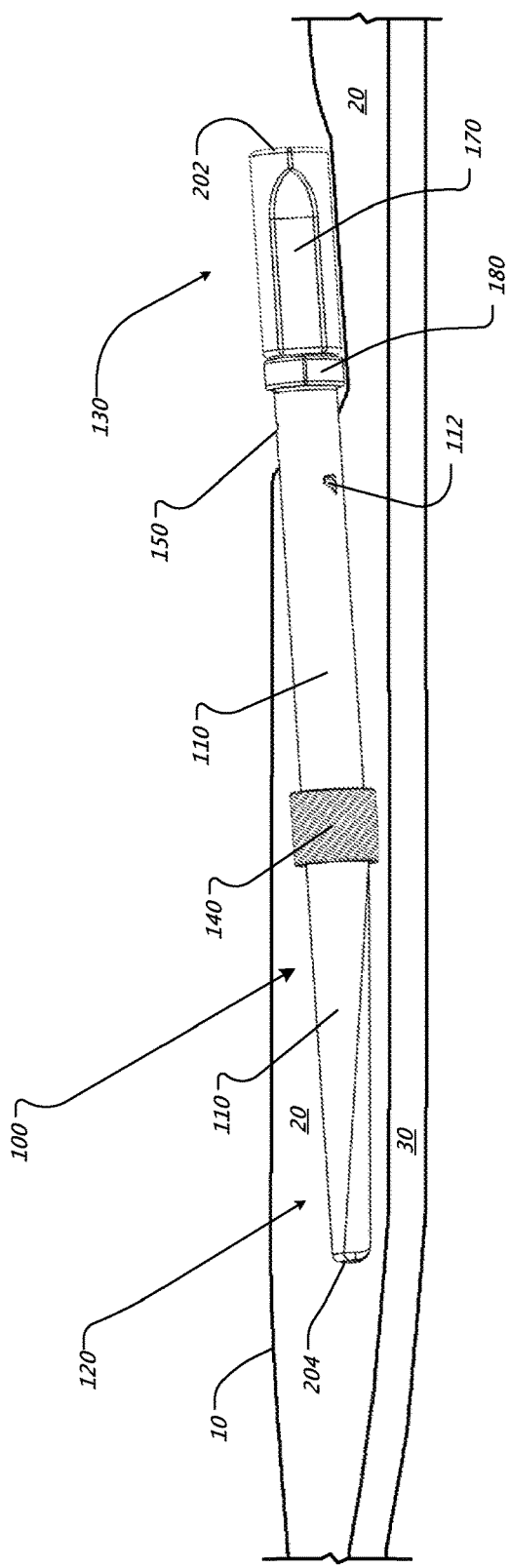
FIG. 7 is a side view of the anchor sleeve device of FIG. 1 being advanced into a subcutaneous region.
Figure 8:
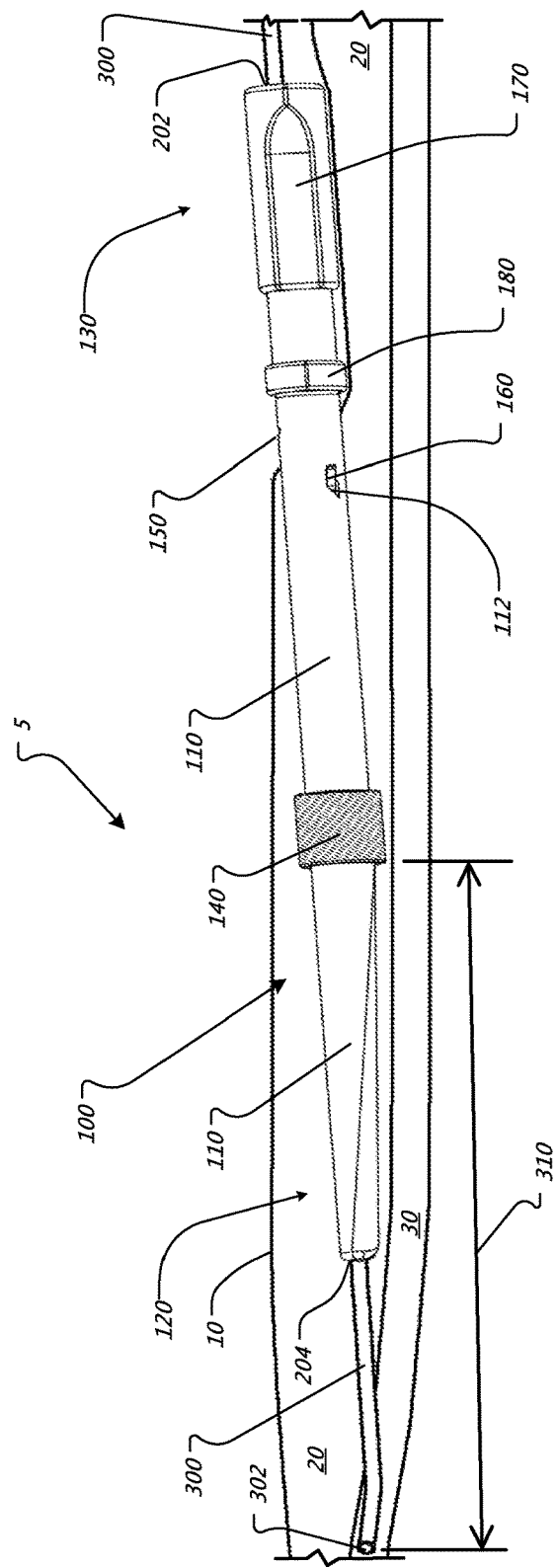
FIG. 8 is another side view of the anchor sleeve device of FIG. 7 having the anchors in a deployed position and having a catheter device passing therethrough.

In some embodiments, the sleeve device 100 may be inserted through a percutaneous opening formed in the skin (e.g., a puncture, an incision, or the like) and into the subcutaneous region so that the cuff 140 rests in the subcutaneous region (refer, for example, to FIGS. 7-8). The cuff 140 may be made of a biocompatible material (e.g., a polyester material such as Dacron, a polytetraflouroethelene material such as a Goretex mesh, titanium mesh, or the like) that is configured to receive the ingrowth of bodily tissue or otherwise embed with the surrounding tissue. As such, the cuff 140 may embed in the subcutaneous tissue over a period of time to limit or prevent the migration of infection from outside the skin to components or anatomical structures (e.g., blood vessels) distal of the cuff 140. After initial insertion of the sleeve device 100 into the subcutaneous region, the subcutaneous anchors 160 may be deployed in the subcutaneous region to assist in retention of the sleeve device 100 in position, thereby permitting the cuff 140 to sufficiently embed over a period of time (refer, for example, to FIG. 8).

In some embodiments, the sleeve device 100 may be used for long-term anchoring of a catheter or other medical instrument in a patient. For example, a chronic dialysis catheter may be advanced through the sleeve device 100 and into a patient requiring ongoing dialysis treatments. The dialysis catheter may reside in the patient's body for a long-term period of weeks or months. The cuff 140 may be designed to function as a long-term anchor instrument and as a barrier for infection, which can be accomplished through tissue ingrowth into the cuff 140. In this embodiment, the cuff 140 comprises a Dacron material, which may include polyester, and may have a porous texture to encourage tissue ingrowth. In alternative embodiments, the cuff 140 may comprise other materials (e.g., Goretex mesh, titanium mesh or the like) suitable for use in the subcutaneous region to encourage tissue ingrowth. In additional embodiments, a combination of biocompatible materials may be used in the cuff 140. Although the sleeve device 100 is shown as having a single cuff 140 in this embodiment, it should be understood from the description herein that more than one cuff can be employed on an outer surface of the sleeve device 100.

In some embodiments, the depth indicator 150 is present on the body 110 of the sleeve device 100 to assist the user in placing the sleeve device 100 to a desired depth in a patient. As described below in connection with FIGS. 7-8, the sleeve device 100 can be inserted through an entry point in the skin into the subcutaneous layer until the depth indicator 150 is adjacent to the epidermis at the skin entry point. In some embodiments, the depth indicator 150 can include one or more indentations in the body 110. In additional embodiments, the depth indicator 150 could be one or more markings indicating the depth at which the sleeve device 100 has been inserted.

Still referring to FIGS. 1-2, the sleeve device 100 includes one or more subcutaneous anchors 160 for use in the temporary anchoring of at least a portion of body 110 in the subcutaneous layer under the skin. In some embodiments, the subcutaneous anchors 160 may comprise a material that exhibits superelasticity when used in the patient's body. As such, the subcutaneous anchors can flexibly shift from a non-deployed position to a deployed position when in the subcutaneous layer. For example, the anchors 60 may be formed from a length of nitinol wire or from a sheet of nitinol material, which has been processed to exhibit superelasticity below or at about a normal human body temperature, such as below or at about 37 degrees C. The nitinol material may comprise, for example, Nickel Titanium (NiTi), Niobium Titanium (NbTi), or the like. Alternatively, the subcutaneous anchors 160 may comprise a metal material such as stainless steel, spring steel, titanium, MP35N and other cobalt alloys, or the like. In these embodiments, the subcutaneous anchors 160 can be formed from a material or materials that allow them to be adjustable from a non-deployed position to a deployed position.

In some embodiments, the subcutaneous anchors 160 can be flexed to a stressed condition when in the non-deployed position (e.g., prior to placement of the sleeve device 100 in a patient). For example, as shown in FIG. 2, the subcutaneous anchors 160 may be retracted into the body 110 when in the non-deployed position. When deployed, as shown in FIG. 1, the subcutaneous anchors 160 can return to a shape (e.g., by exhibiting superelastic characteristics) that allows the subcutaneous anchors 160 to at least temporarily retain a portion or all of the body 110 in the subcutaneous region for a period of time until tissue has properly adhered to the cuff 140. The subcutaneous anchors 160 may be designed with a curvature that facilitates the transition from the non-deployed to the deployed position. Furthermore, the curvature of the anchors 160 may be configured to eliminate or reduce the potential damage done to the skin during deployment of the anchors 160. For example, the anchors 160 may include a convex curvature that abuts against the underside of the skin in a manner that prevents the tips of the anchors 160 from piercing through the skin.

In use, the subcutaneous anchors 160 can be shifted to the non-deployed position (refer, for example, to FIG. 2) prior to insertion so as to minimize resistance and possible damage to the skin when inserted through the skin entry point. When the anchor sleeve device 100 has been inserted to the intended depth inside the subcutaneous layer, the anchors 160 can be shifted to the deployed position (refer, for example, to FIG. 1) to provide at least temporary anchoring for some or all of the anchor sleeve device 100. When removal of the anchor sleeve device 100 is desired, the subcutaneous anchors can be shifted to the non-deployed position prior to removal to minimize resistance and possible damage to the skin and subcutaneous region.

As shown in FIG. 2, the actuator 170 can be adjusted relative to the body so as to cause the subcutaneous anchors 160 to retract to the non-deployed position. In this embodiment, the actuator 170 can be depressed until it contacts the stopper 180 causing the subcutaneous anchors 160 to retract into the body 110. Transitioning the subcutaneous anchors 160 from the deployed position (FIG. 1) to the non-deployed position (FIG. 2) can allow for easier insertion of the anchor sleeve device 100 into a subcutaneous region through the skin entry point. After the sleeve device 100 is inserted into the patient, the actuator 170 can be shifted away from the stopper 180 to urge the subcutaneous anchors 160 to extend from the body 110 (as shown in FIG. 1). In some embodiments, the anchors 160 can then act as temporary anchor for the sleeve device 100 for a period of time to allow the surrounding tissue to properly adhere to the cuff 140.

Figure 3:
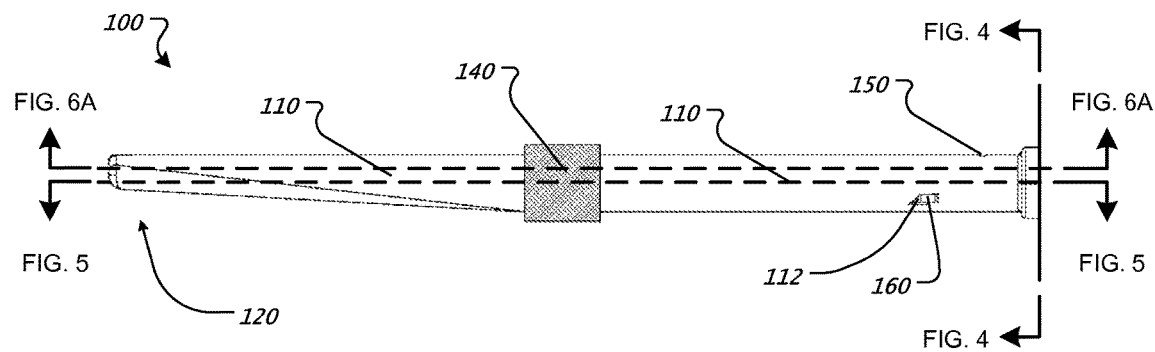
FIG. 3 is a side view of a portion of the anchor sleeve device of FIG. 1.
Figure 4:
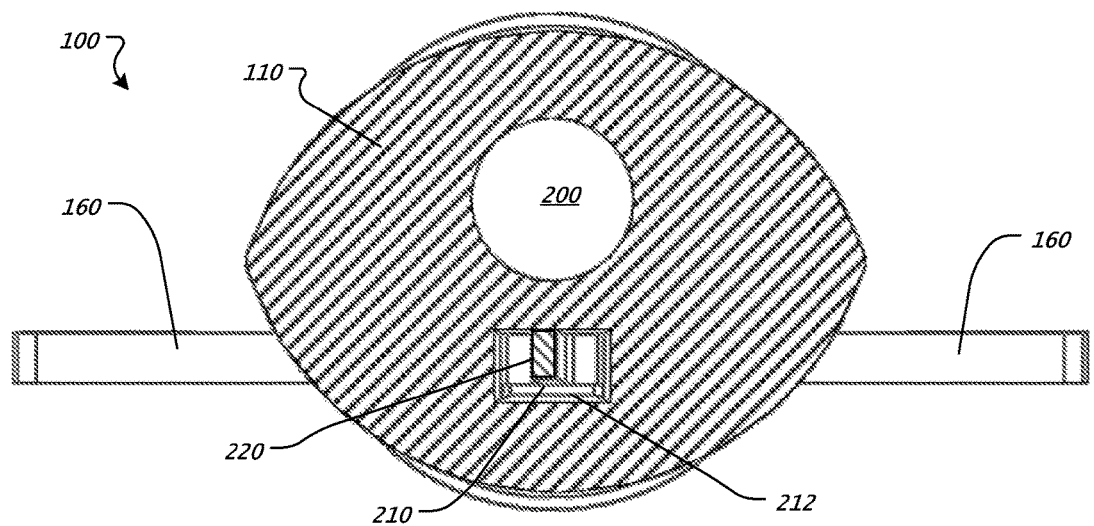
FIG. 4 is a cross-sectional view of the anchor sleeve device of FIG. 3.

Referring now to FIGS. 3-4, the body 110 of the sleeve device 100 may have an elongate shape and can comprise a biocompatible material, such as PEEK (polyetheretherketone), polyethylene, polyimide, or the like. The body 110 may have a modified elliptical cross-sectioned shape (as shown, for example, in FIG. 4) and may include a taper along the distil portion 120 that facilitates insertion of the sleeve device 100 through the skin of a patient. In this embodiment, the previously described cuff 140 is located on the body 110 adjacent to this taper (as shown in FIG. 3). Alternatively, the cuff 140 may be located along the tapered region closer to the distal tip, or may be located in a more proximal position closer to the anchors 160. As shown in FIG. 3, the body 110 may also include anchor holes 112 through which the anchors 160 extend when deployed.

Referring to FIG. 4, in some embodiments, the sleeve device 100 can include one or more internal channels 200 and 210. For example, the sleeve device 100 may include a working channel 200 to receive a catheter or other medical instrument, and may also include an actuator channel 210 to accommodate the actuation of the subcutaneous anchors 160.

The working channel 200 can extend through the entire length of the sleeve device 100 from the distal tip portion 120 to the proximal portion 130. After insertion of at least a portion of the body 110 into a subcutaneous region, the working channel 200 can be used to introduce a catheter or other medical instrument into a patient. Thus, the catheter can be introduced into the working channel 200 at the proximal portion 130 and inserted through the entire body 110 of the sleeve device 100 until it emerges from the distil tip portion 120.

In the embodiment depicted in FIG. 4, the sleeve device 100 contains a single, round working channel 200. In alternate embodiments of the sleeve device 100, the working channel 200 need not be round or of the size depicted. For example, the working channel 200 may have a cross-sectional shape in the form of a square or other polygon that mates with the medical instrument to be passed therethrough. Also, the working channel 200 need not be a single lumen. In alternate embodiments, the sleeve device 100 may include multiple working channels, such as adjacent channels or coaxial channels that permit the introduction of multiple medical instruments (e.g., catheters, endoscopes, or the like). Furthermore, the multiple working channels may be selectively sealable so that one working channel could be accessed while another is sealed. In such cases, it would be possible to introduce and secure several catheters at different points in time.

Still referring to FIGS. 3-4, the actuator channel 210 of the sleeve device 100 is formed in the body 110 and can movably receive an actuator rod 220. The actuator channel 210 may be defined by one or more side walls 212 that can slidably engage the actuator rod 220. Movement of the actuator rod 220 within the actuator channel 210 can urge the anchors 160 to extend from, or retract into, the actuator channel 210. In this embodiment, the cross-sectional shape of the actuator rod 220 may be that of a quadrilateral to permit longitudinal movement of the actuator rod 220 while hindering the rotational movement of the actuator rod 220 about its longitudinal axis. While this embodiment of the anchor sleeve 100 contains an actuator channel 210, other embodiments may have non-adjustable anchors or no anchors at all (refer, for example, to FIGS. 9-11) and as such may not include an actuator channel 210 or related components.

Figure 5:
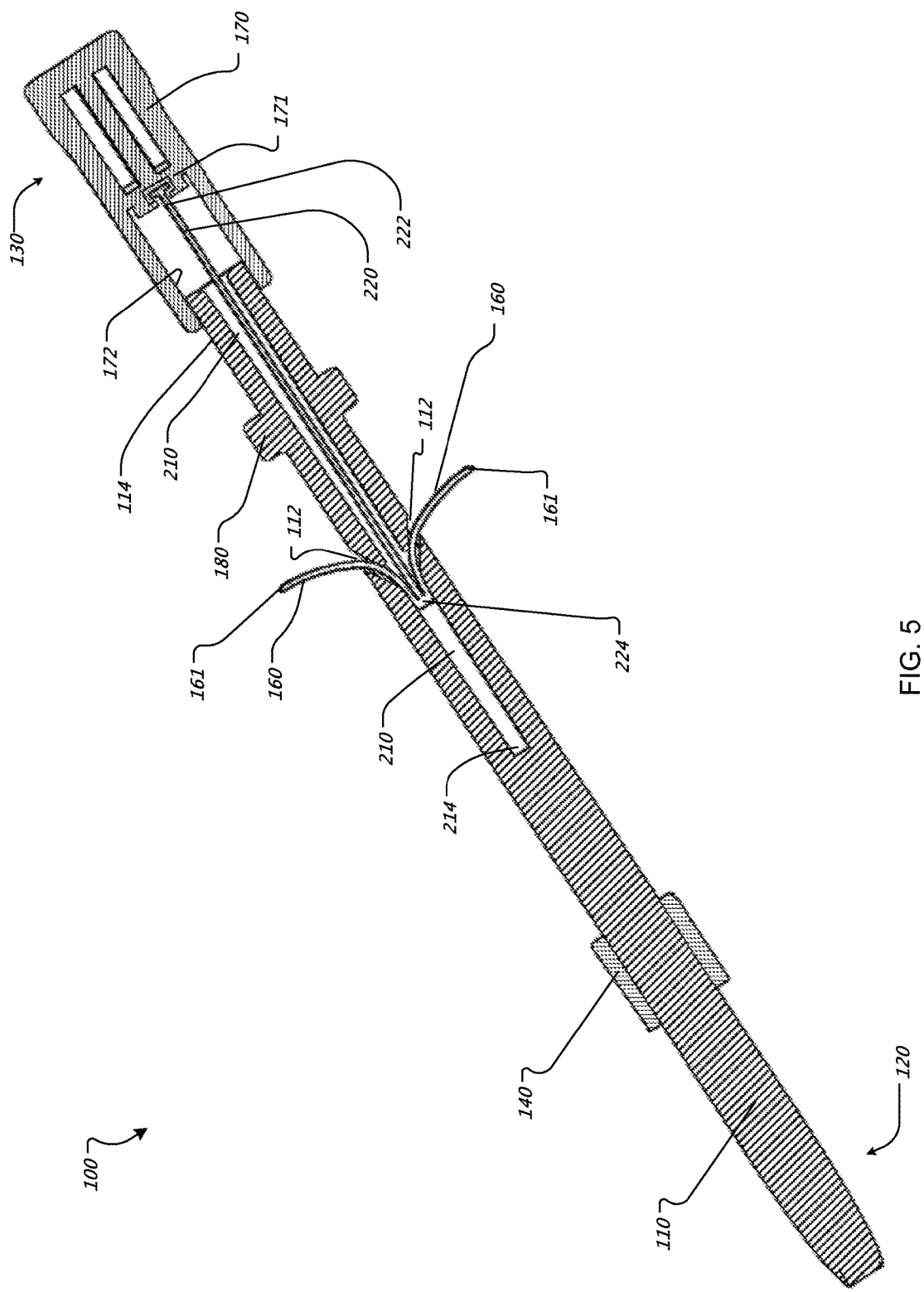
FIG. 5 is another cross-sectional view of the anchor sleeve device of FIG. 3.

Referring now to FIG. 5, the actuator rod 220 of the sleeve device 100 can be reciprocated within the actuator channel 210 in the longitudinal direction of the sleeve device 100. The actuator rod 220 may include a proximal end 222 that is coupled to the actuator 170 via, for example, a connector portion 171 of the actuator 170. As such, movement of the actuator 170 can be translated to the actuator rod 220. The actuator 170 can be slidably engaged with the body 110 and may include a circumferential inner wall 172 that can slidably mate with a circumferential outer wall 114 of the body 110. When the actuator 170 is moved relative to the body 110, the inner wall 172 and the outer wall 114 may stay in contact such that a seal is maintained against the transfer of liquids. The actuator rod 220 has a distal end 224 that can be advanced and retracted within the actuator channel 210 in response to the movement of the actuator 170. The anchors 160 can be coupled to the actuator rod 220 such that movement of the actuator 170 (and the corresponding translation of the actuator rod 220 within the actuator channel 210) causes the anchors 160 to shift between the non-deployed position and the deployed position. In this embodiment, the anchors 160 are integrally formed with the actuator rod 220 (e.g., formed from a nitinol material or the like).

The actuator channel 210 may not extend fully through the body 110 of the anchor sleeve 100. For example, the actuator channel 210 may extend from the proximal portion 130 to a depth that extends to a terminal end 214. In some embodiments, when the actuator 170 is pressed against the stopper 180, the anchor actuator rod 220 is caused to advance within the anchor actuator channel 210 such that the distal end 224 of the actuator rod 220 approaches the terminal end 214 of the actuator channel 210. In this embodiment, the anchors 160 are coupled to the actuator rod 220 so that the anchors 160 retract into the body 110 as the distal end 224 of the rod 220 approaches the terminal end 214 (shifts to the non-deployed state). In such circumstances, the anchors 160 may be flexed to a stressed condition while retained within the actuator channel 210.

It should be understood from the description herein that, in some embodiments, the anchors 160 can be joined with the actuation rod 220 at a location other than the distal end 224. For example, in other embodiments, the anchors 160 may be connected to the actuator rod 220 along a middle region of the rod 220. Also, in alternative embodiments, the anchors 160 may be non-integral with the actuator rod 220. For example, the anchors may be formed separately from the actuator rod 220 and then mounted to the rod 220 using an adhesive, a weld, a connector, or the like.

As shown in FIG. 5, the actuator 170 can be pulled back from the stopper 180, and this movement is translated to the actuator rod 220 via the connector portion 171. The actuator rod 220 slides within the actuator channel 210 so that the distal end 224 of the rod shifts away from the terminal 214. This motion of the actuator rod 220 causes the distal tips 161 of the anchors 160 to pass through the openings 112 and thereby extend outwardly from the body 110. It should be understood from the description herein that, in alternative embodiments, the actuator rod 220 and anchors 160 could be configured so that pulling the actuator 170 in the direction away from the stopper 180 would cause the anchors 160 to transition to their non-deployed state, while pressing the actuator 170 in the direction of the stopper 180 would cause the anchors 180 to transition to the deployed state.

Referring now to FIG. 6A, the working channel 200 can extend through the length of the sleeve device 100 and can receive at least one catheter or other medical instrument. In some embodiments, the working channel 200 can have a diameter of about 3 French to about 30 French, and about 5 French to about 20 French, including particular ranges from about 3 French to about 7 French and about 12 French to about 17 French. As such, the working channel 200 can accept a wide range of catheters and medical instruments. The working channel 200 can extend from a proximal opening 202 located in the proximal portion 130 of the sleeve 100 to a distal opening 204 located in the distil tip portion 120 of the sleeve 100. When a catheter or other medical instrument is inserted into the sleeve device 100, it enters the working channel 200 via the proximal opening 202, travels through an opening 116 in the body 110, continues to travel down the working channel 200 until emerging from the distal opening 204.

In some embodiments, the actuator 170 is slidably engaged with the body 110 such that the actuator 170 may move longitudinally relative to the stopper 180. The sleeve device 100 may include a locking device 174 that can be adjusted to clamp to, or otherwise connect with, the catheter passing through the working channel 200. As such, the locking device 174 serves as a mechanism that releasably secures the catheter to the sleeve device 100 after the catheter has been advanced through the sleeve device 100 toward a targeted location. In some circumstances, the locking device 174 can also form a seal around the catheter when connected thereto. As described in more detail below in connection with FIG. 6B, locking device 174 can include one or more components that extend from the proximal face 118 of the sleeve body 110. In addition, the locking device 174 may also include side walls 178 which slidably engage an inner walls 179 of the actuator 170, thus creating a dynamic seal as the actuator 170 moves longitudinally relative to the body 110.

Referring now to FIG. 6B, some embodiments of the locking device 174 may include first and second jaws 175a-b that operate to clamp upon the outer surface of the catheter when the catheter is position in the working channel 200. (It should be understood that the catheter and the actuation rod 220 have been removed from view in FIG. 6B for purposes of illustrating the locking device 174). For example, the first and second jaws 175a-b can compress the catheter into a locking engagement in response to movement of the actuator 170. As such, the catheter can be advanced through the working channel 200 to a targeted location inside the patient's body. Thereafter, the actuator 170 can be shifted away from the stopper 180 so as to deploy the anchors 160 (as previously described in connection with FIG. 5). This movement of the actuator 170 can also cause the second jaw 175b to shift relative to the first jaw 175a so as to compress the outer surface of the catheter (or other medical instrument) disposed in the working channel 200.

In this embodiment, the first jaw 175a is a fixed component that extends from the proximal surface 118 of the sleeve body 100. For example, the first jaw 175a may be integrally formed with the sleeve body 100. The second jaw 175b is adjustable relative to the first jaw 175a so as to provide a clamping action or other locking operation. For example, the second jaw 175b can extend from the proximal surface 118 so as to be cantilevered from the sleeve body 110. The second jaw 175b may include at least one cam surface 176a that slidably engages a guide member 177 of the actuator 170. The cam surface 176a can include a decline path or other configuration that causes the guide member 177 to force the second jaw 175b toward the first jaw when the actuator 170 (and the guide member 177) are moved away from the stopper 180. Thus, the motion of the actuator 170 causes the guide member 177 to act upon the cam surface 176a and shift the second jaw 175b toward the first jaw 175a, thereby causing the jaws 175a-b to clamp or otherwise lock onto the medical instrument inside the working channel 200.

It should be understood that, in some embodiments, the locking device 174 may include one or more seal members arranged between the opposing surfaces of the jaws 175a-b. For example, a silicone seal having a half-cylinder shape can be affixed to the inner cylindrical face of the first jaw 175a, and an opposing silicone seal having a half-cylinder shape can be affixed to the inner cylindrical face of the second jaw 175b. As such, when the second jaw 175b is forced toward the first jaw 175a, the opposing seal members would surround and compress the outer surface of the catheter arranged in the working channel 200. In such embodiments, the locking device 174 can form a seal around the catheter in addition to locking the catheter to the sleeve device 100.

Still referring to FIG. 6B, the guide member 177 may be stopped at the end of its travel by a notch 176b formed in the second jaw 175b. The notch 176b can be configured to mate with the guide member 177 so that further longitudinal movement of the guide member 177 (and the actuator 170) is inhibited. In this embodiment, notch 176b releases the guide member 177 when the actuator 170 is moved in a return path toward the stopper 180. In such circumstances, the guide member 177 moves along the cam surface 176a so that the second jaw 175b can pivot away from the first jaw 174a, thereby releasing the catheter from the locking engagement with the sleeve device 100.

Referring now to FIG. 7, in some embodiments, the sleeve device 100 may be inserted through a hole in skin 10 of a patient until at least a portion of the body 110 is located in a subcutaneous region 20. In preparation for insertion, the actuator 170 may be pressed against the stopper 180 to retract the anchors 160 through the anchor holes 112 and into the non-deployed position inside the body 110. In particular embodiments, the sleeve device 100 can be introduced through a patient's skin prior to commencement of a medical procedure or other treatment. For example, the sleeve device 100 may penetrate the skin 10 and subcutaneous region 20 through a small incision made by a physician. In some cases a dilation instrument may be used to assist in advancing the sleeve device 100 through the incision.

In some embodiments, once the sleeve device 100 has been inserted through the skin 10, at least a portion of the body 110 may be located inside the subcutaneous region 20. In this example, the sleeve device 100 is inserted such that, for example, the distal tip portion 120, the cuff 140, and the anchor holes 112 are located inside the subcutaneous region 20. In particular, the anchors holes 112 can be positioned in the subcutaneous region 20 proximate to the underside of the skin 10. As such, the actuator 170, the stopper 180, and the proximal opening 202 remain external to the skin so that a practitioner has access to the proximal opening 202 (e.g., to insert the catheter) and the actuator 170 (e.g., to shift the anchors 160). The sleeve device 100 can be positioned such that the distal opening 204 is adjacent to a targeted blood vessel 30 or other body lumen that will receive the catheter or other medical instrument passing through the sleeve 100.

Referring to FIG. 8, after the sleeve device 100 has been placed such that at least a portion of the body 110 (e.g., the distal tip portion 120, the cuff 140, and the anchor holes 112) is in the subcutaneous region 20, the sleeve device 100 can be anchored at least temporarily through the use of the deployed anchors 160. To deploy the anchors 160, the actuator 170 can be shifted in a proximal direction away from the stopper 180. In doing so, the anchors 160 are transitioned from the non-deployed position inside the body 110 to the deployed position outside of the body 110 by extending out of the anchor holes 112. As the anchors 160 extend through the anchor holes 112, they transition from their stressed shape inside the body 110 to their memory shape (e.g., curved shape in this example). When the anchors 160 extend from the anchor holes 112, which are positioned just under the skin 10 in the subcutaneous region 20, the curved shape of the anchors 160 can allow them to deploy adjacent to the skin 10 without tearing or otherwise damaging it. When deployed, the anchors 160 can exert a retainment force on the body 110 that secures the position of the sleeve device 100 relative to the skin entry point. In some embodiments, the anchors 160 may provide a holding force of about 1 lb. or greater, depending upon the medical procedure being performed, the materials comprising the anchors 160, the geometry of the anchors 160, and/or other factors. For example, the anchors 160 may provide a holding force of about 0.5 lbs or more, about 1 lb to about 20 lbs, about 1 lb to about 5 lbs, or about 2 lbs to about 3 lbs.

In some embodiments, while the anchors 160 are serving as a temporary or long-term device for retaining the sleeve device 100, some bodily tissue can grow into or otherwise embed with the cuff 140 over a period of time. When embedded with the surrounding bodily tissue, the cuff 140 can serve as a long-term anchor for the sleeve device 100, either in lieu of the anchors 160 or as a supplement to the anchors 160. Furthermore, the cuff 140 can act as a barrier against infection, for example, by minimizing the transmittance of bacteria from the external surface of the skin 10 to underlying anatomical structures, such as the blood vessel 30. In some embodiments, after a period of time has elapsed which is long enough for tissue to have grown into the cuff 140, the anchors 160 may be transitioned back to their non-deployed position, thus no longer utilizing the anchors 160 to secure the sleeve device 100 in place. Alternatively, the anchors 160 may be left in their deployed position to act as an additional long-term anchor point for the sleeve device 100.

Still referring to FIG. 8, the sleeve device 100 can be operated as part of a system 5 including the sleeve device 100 and another medical instrument. When the sleeve device 100 has been inserted in the subcutaneous region 20 and has been anchored there (e.g., by the anchors 160, the cuff 140, or a combination thereof), a medical instrument, such as a catheter 300, can be introduced through the working channel 200 (FIGS. 4 and 6) and into the body. For example, the catheter 300 can be inserted into the working channel 200 of the sleeve device 100 at the proximal opening 202, and can continue to be advanced until it emerges from the distal opening 204 along the distal tip portion 120. In the example depicted in FIG. 8, the catheter 300 can continue to be advanced toward a penetration location into a targeted blood vessel 30. As the sleeve device 100 and cuff 140 remain in place relative to the patient, the catheter 300 can be advanced until the catheter tip 302 reaches a targeted site within the body. Accordingly, the distance between the cuff 140 and the catheter tip 302 (e.g., the tip-to-cuff distance 310) can be selectively adjusted depending on the patient's size, the patient's anatomy, the intended medical treatment, and other factors.

Advantageously, because the position of the catheter tip 302 is adjustable relative to the position of the sleeve device 100, the tip-to-cuff distance 310 can be selected by the practitioner while the catheter tip 302 is advanced through the patient's body. Also, the tip-to-cuff distance 310 is adjustable at the time of insertion, so this distance need not be determined prior to the start of the procedure. Furthermore, such a system 5 that provides the adjustable tip-to-cuff distance 310 can reduce the need for hospitals or clinics to inventory a wide assortment of cuff-attached catheters, each having a non-adjustable tip-to-cuff length. Moreover, due to the adjustable nature of the tip-to-cuff distance 310, the practitioner is not required to trim the distal portion of a catheter to achieve the desired dimensions, thereby by reducing the risk of over-shortening the catheter or altering features of the catheter tip.

Figure 9:
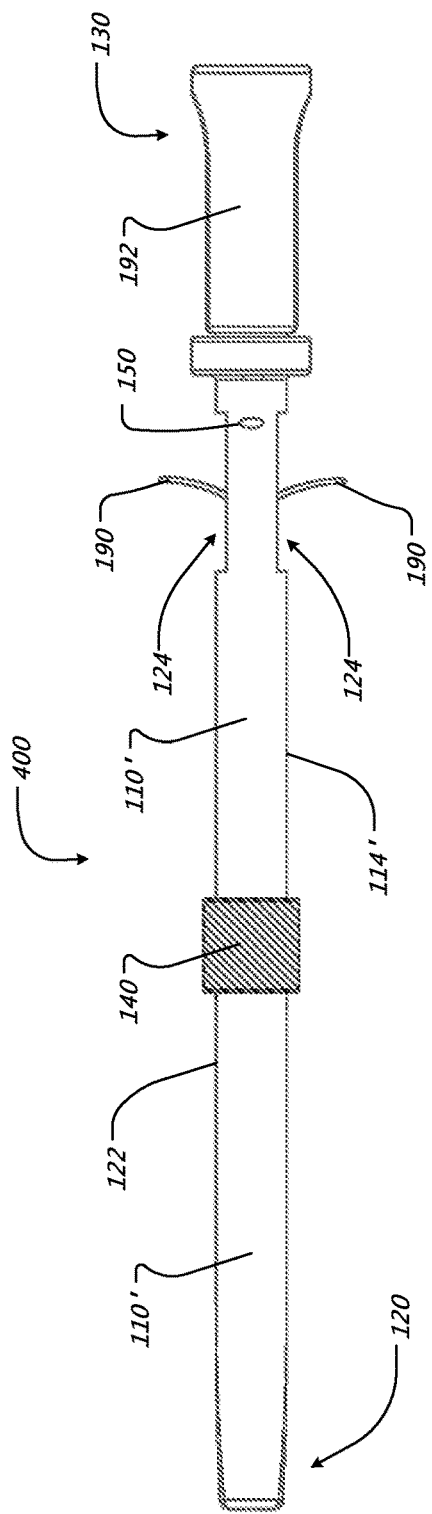
FIGS. 9-10 are top and side views of an anchor sleeve device having non-retractable anchors, in accordance with some embodiments.

Referring to FIG. 9, some alternative embodiments the sleeve device 400 may include anchors 190 that do not retract into openings in the elongate body. For example, the anchors 190 may be designed to flex to a position against the side of the elongate body 110' during insertion through the skin and then to elastically return to a deployed position (e.g., a curved shape in this example) after entering into the subcutaneous region. In the depicted embodiment, the sleeve device 400 includes two flexible, non-retractable anchors 190 that comprise a bio-compatible polymer material capable of elastically flexing during insertion into the subcutaneous region and capable of elastically flexing or plastically deforming during removal from the patient's skin. Similar to previously described embodiments, the anchors 190 can a material that exhibits superelasticity (e.g., Nitinol or the like). The anchors 190 can be deployed in the subcutaneous region so as to at least temporarily retain the anchor sleeve 400 in engagement with the patient's body while the cuff device embeds with the surrounding tissue over a period of time. In some embodiments, the anchors 190 may have grooves or notches formed therein to facilitate the proper flexing or deformation during insertion into the subcutaneous region or removal from the patient's skin, as described in more detail below. In these examples, the anchors 190 are not adjusted by an actuator, so the sleeve device 400 may not include, for example, an actuator channel 210, an activation rod 220, or an actuator 170 (as previously described in connection with FIG. 5). In these embodiments, the sleeve device 400 can include one or more working channels 200 to receive a number of medical instruments. Furthermore, the sleeve device 400 may include a stationary handle 192 to assist in the insertion and removal of the sleeve device 400 from a patient.

In some embodiments, the anchors 190 may extend away from the plane of the outer wall 114' of the body 110'. As shown in FIG. 9, some embodiments of the body 110' may comprise one or more wall pockets 124 to receive the anchors 190 in the event they are flexed to a non-deployed position against the body 110' (e.g., during insertion or extraction from a patient). In these embodiments, the wall pocket 124 may serve to reduce the likelihood of trauma to the patient's skin during insertion by providing a space to accommodate one or more of the anchors 190. When the sleeve device 400 is inserted into a patient, the anchors 190 may flex into a proximal region of the wall pocket 124 as they pass through the entry hole in the skin. Once the sleeve device 400 is inserted such that at least a portion of the body 110 (e.g., including the distal tip portion 120 and the cuff 140) and the anchors 190 are located in the subcutaneous region 20, the sleeve device 400 is in position such that the anchors 190 may return a deployed position similar to that shown in FIG. 9. When the sleeve device 400 is removed from a patient, the anchors 190 are configured to elastically flex or plastically deform into a distal region of the wall pocket 124 as they exit from the hole in the skin.

Still referring to FIG. 9, the sleeve device 400 can include a number of features that are similar to the previously described embodiments. For example, the sleeve device 400 can include the cuff 140 and the depth indicator 150 arranged on the elongate body 110'. The sleeve device 400 may also include one or more working channels 200. In some circumstances, the sleeve device 400 may include the working channel 200 as described in connection with FIGS. 6A-B and other related features (e.g., the distal opening 204) so as to receive a medical instrument such as a catheter 300.

Figure 10:
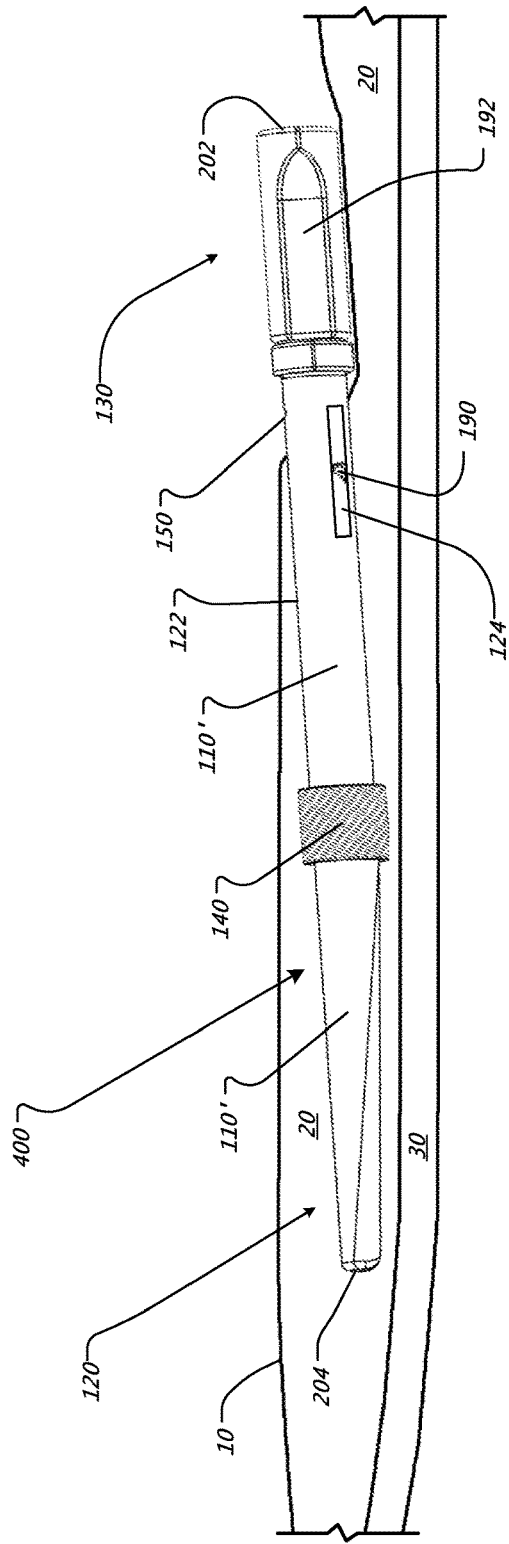

Referring now to FIGS. 9-10, the sleeve device 400 may be introduced into a patient so that the anchors 190 may releasably secure at least a portion of the body 110 in the subcutaneous region 20 of a patient. The insertion force applied to the body 110' may cause at least a portion of the anchors 190 to flex during insertion through the skin entry point. For example, each anchor 190 may superelastically flex toward a proximal region of the pocket 124 during insertion, and then can return to the deployed position (e.g., having a curved shape in this embodiment) when arranged in the subcutaneous region 20. In the event the sleeve device 400 is to be removed from the subcutaneous region 20, the removal force applied to the body 110' may cause at least a portion of the anchors 190 to flex or deform toward a distal region of the wall pockets 124. Thus, the anchors 190 may be self-actuated without the need for a separate actuation device (e.g., the actuator rod 220, or the like) to extend or retract the anchors 190.

In some embodiments, the sleeve device 400 may be introduced through a patient's skin prior to commencement of a medical procedure or other treatment. For example, the sleeve device 400 may be advanced through the skin 10 and into the subcutaneous region 20 via a small incision made by a physician. In some cases a dilation instrument may be used to assist in advancing the sleeve device 400. As a result of an insertion force applied to the sleeve device 400 by the physician, the anchors 190 may be temporarily flexed from their unstressed configuration (as shown, for example, in FIG. 9) to a proximally oriented configuration in which the anchors 190 extend substantially in a direction along the wall pockets 124 of the body 110'. Such flexing action permits at least a portion of the anchors 190 to enter through the incision with a reduced likelihood of traumatizing the skin around the incision.

As shown in FIG. 10, after the anchors 190 have passed through the skin 10, the anchors 190 can return partially or fully toward the unstressed configuration (as shown, for example, in FIG. 9) so as to deploy within the subcutaneous region 20. For example, the subcutaneous region 20 may comprise fatty tissue in which the anchors 190 can move in a sweeping arcuate motion away from the body 110'. Such deployment in the subcutaneous region 20 can releasably secure the sleeve device 400 to the patient's body for a period of time while the cuff 140 embeds with the surrounding tissue (as previously described). In this embodiment, the anchors 190 extend away from the outer wall 114' of the body 110' with a curvature so that the tips of the anchors 190 are not necessarily pointed at the underside of the skin 10. Such a configuration may be accomplished, for example, by inserting the anchors 190 further into the subcutaneous region 20 and then moving the anchors 190 with a slight pulling motion to permit the anchors 190 to sweep outwardly from the body 110'. It should be understood that, due to the vagaries of human anatomy and differing inward and outward forces during treatment, in some embodiments the orientation and position of the deployed anchors 190 may vary when deployed in the subcutaneous region 20. In some embodiments, the anchors 190 may provide a holding force of about 1 lb. or greater, depending upon the medical procedure being performed, the materials comprising the anchors 190, the geometry of the anchors 190, and/or other factors. For example, the anchors 190 may provide a holding force of about 0.5 lbs or more, about 1 lb to about 20 lbs, about 1 lb to about 5 lbs, or about 2 lbs to about 3 lbs.

In some embodiments, once the sleeve device 400 has been inserted through the skin 10, at least a portion of the body 110 may be located inside the subcutaneous region 20. In this example, the sleeve device 400 is inserted such that, for example, the distal tip portion 120, the cuff 140, and the anchors 190 are located inside the subcutaneous region 20, and the handle 192 remains external to the patient. Similar to previously described embodiments, the sleeve device 400 can be positioned such that the distal opening 204 is near to a blood vessel 30 and the proximal opening 202 is external to the patient so as to receive a catheter 300 (FIG. 8) or other medical instrument. As previously described in connection with FIG. 8, the distance between the cuff 140 and the catheter tip can be selectively adjusted depending on the patient's size, the patient's anatomy, the intended medical treatment, and other factors.

Still referring to FIG. 10, the sleeve device 400 may be removed by applying a removal force applied to the sleeve device 400 that overcomes the retainment force. In such circumstances, the anchors 190 may be flexed or deformed from their deployed configuration (as shown, for example, in FIG. 9) to a distally oriented configuration in which the anchors 190 extend substantially in a direction along the wall pockets 124 of the body 110. Such flexing action permits at least a portion of the anchors 190 to exit through the incision in the patient's skin with a reduced likelihood of traumatizing the skin around the incision. For example, the anchors 190 may have a curved configuration in which the tips do not point directly at the skin 10) when deployed in the subcutaneous region 20. As such, the removal force causes the anchors 190 to flex or deform (rather than substantially tear through the underside of the skin 10) in a generally sweeping motion toward the distally oriented configuration. In the embodiments in which the anchors 190 comprise a nitinol material exhibiting superelastic characteristics, the anchors 190 can return toward the unstressed configuration (as shown, for example in FIG. 10) following removal of the sleeve device 100 from the skin. In some alternative embodiments, the anchors 190 may comprise a biocompatible polymer material that can be elastically or plastically deformed into the distally oriented configuration as a result of the removal force applied to the sleeve device 100.

Figure 11:
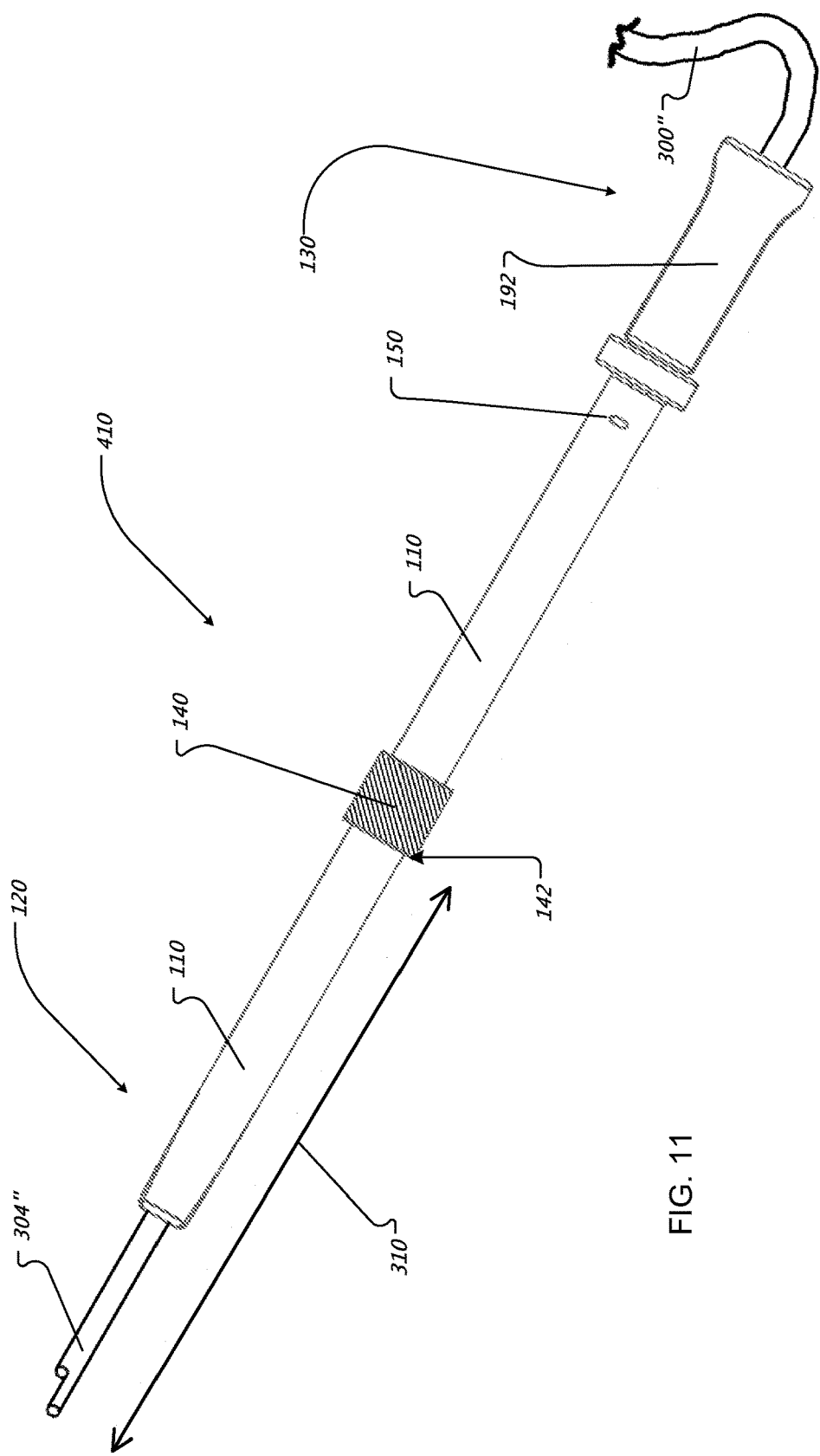
FIG. 11 is a perspective view of an anchor sleeve device having no anchor tines, in accordance with some embodiments.

Referring to FIG. 11, some alternative embodiments of the sleeve device 410 may not include anchors 160 or 190. For example, the sleeve device 410 may be inserted through a hole in the patient's skin (as previously described) to a targeted position within the subcutaneous region 20. In such circumstances, the distal tip portion 120 and the cuff 140 can be located in the subcutaneous region, while the handle 192 remains external to the patient. The sleeve device 410 can be positioned such that the distil opening 204 is near to a blood vessel and the proximal opening 202 is external to the patient such that it can accept a catheter 300" or other medical instrument. Once in position, the sleeve device 410 may receive a temporary retainer (e.g., medical tape, stitches, or the like) to maintain the sleeve device 100 in a desired position for a period of time until the cuff 140 embeds with the surrounding tissue (as previously described) to thereby create a long-term anchor. In addition, the cuff 140 can provide a barrier to infection, as previously described.

In some embodiments, after placement of the sleeve 410 in a patient, a dual lumen catheter 300" with a staggered tip 304" can be introduced into the working channel 200 of the sleeve device 410. For example, the catheter 300" can be inserted into the proximal opening 202, and can continue to be advanced until it emerges from the distil tip portion 120. As with previously described embodiments, the tip-to-cuff distance 310 between the cuff 140 and the catheter tip 304" can be selectively adjusted by a practitioner while the catheter tip 304 is advanced in the patient's body.

Figure 12:
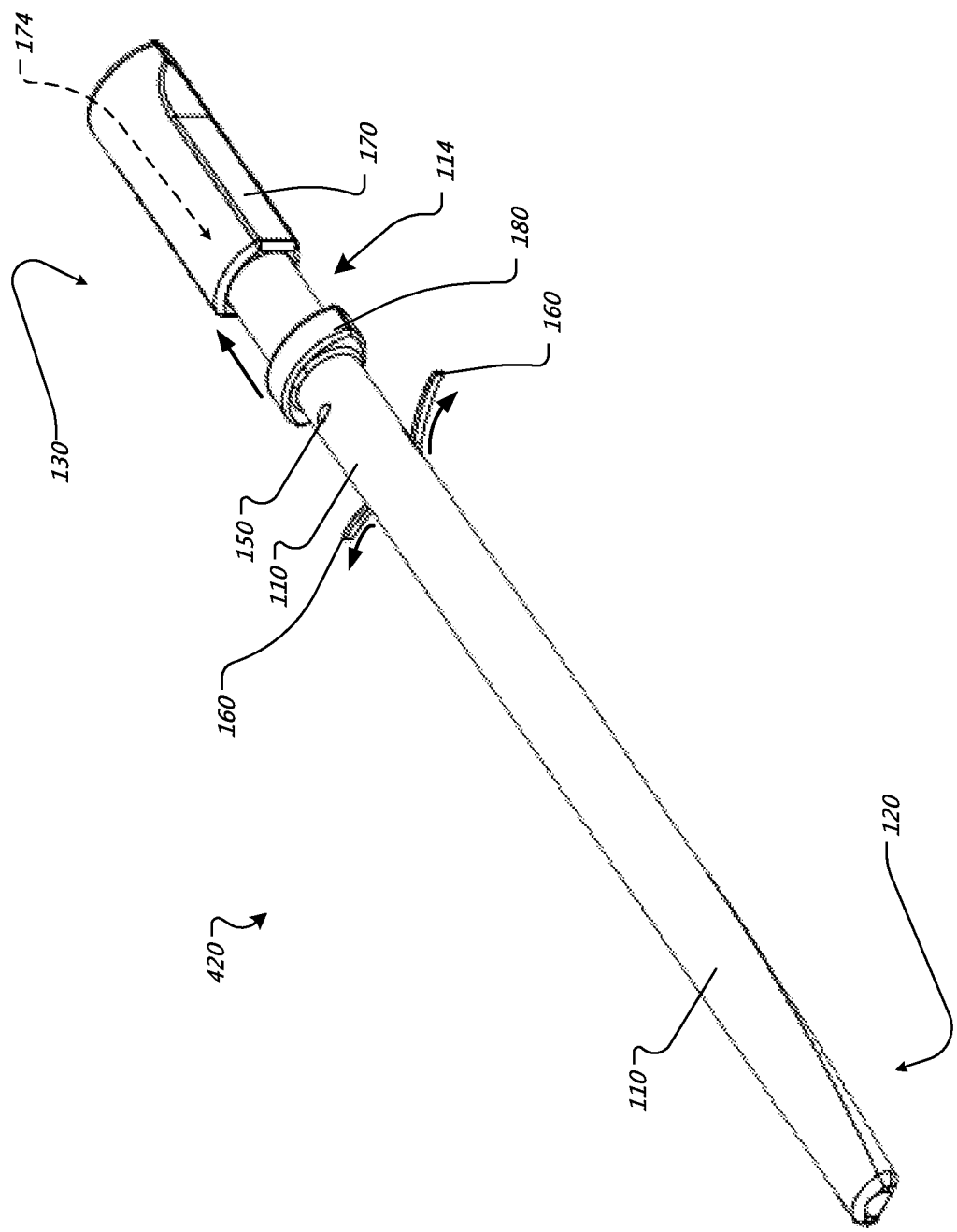
FIG. 12 is a perspective view of an anchor sleeve device having no cuff device, in accordance with some embodiments.

Referring to FIG. 12, some alternative embodiments of the sleeve device 420 may employ the anchors 160 without the subcutaneous cuff device 140 arranged on the sleeve body 110. In such circumstances, the anchor sleeve device 420 may include the actuator 170 that adjust the anchors 160 from a non-deployed position (e.g., retracted inside the sleeve body 110) to the deployed position inside the subcutaneous region 20. As previously described in connection with FIG. 6B, the sleeve device 420 may include a locking device 174 that is shifted when the actuator 170 is moved to deploy the anchors 160. Although the subcutaneous cuff device 140 is not included on the body 110 in this particular embodiment, the anchors 160 can be deployed into the subcutaneous region to retain the sleeve device 420 to the patient's body while the catheter or other medical instrument is passed through the working channel 200 and into the targeted site in the patient's body. Thus, the user can readily operate the actuator 170 is a single motion that contemporaneously deploys the anchors 160 in the subcutaneous region and locks the sleeve body 110 to the catheter or other medical instrument. Furthermore, as previously described in connection with FIG. 6B, the locking device 174 can also form a seal around the catheter when compressed thereon. In such circumstances, the motion of the actuator 170 can cause the anchors 160 to deploy in the subcutaneous region and also cause the sleeve body 110 to lock with and seal around the catheter that resides in the working channel 200.

Figure 13:
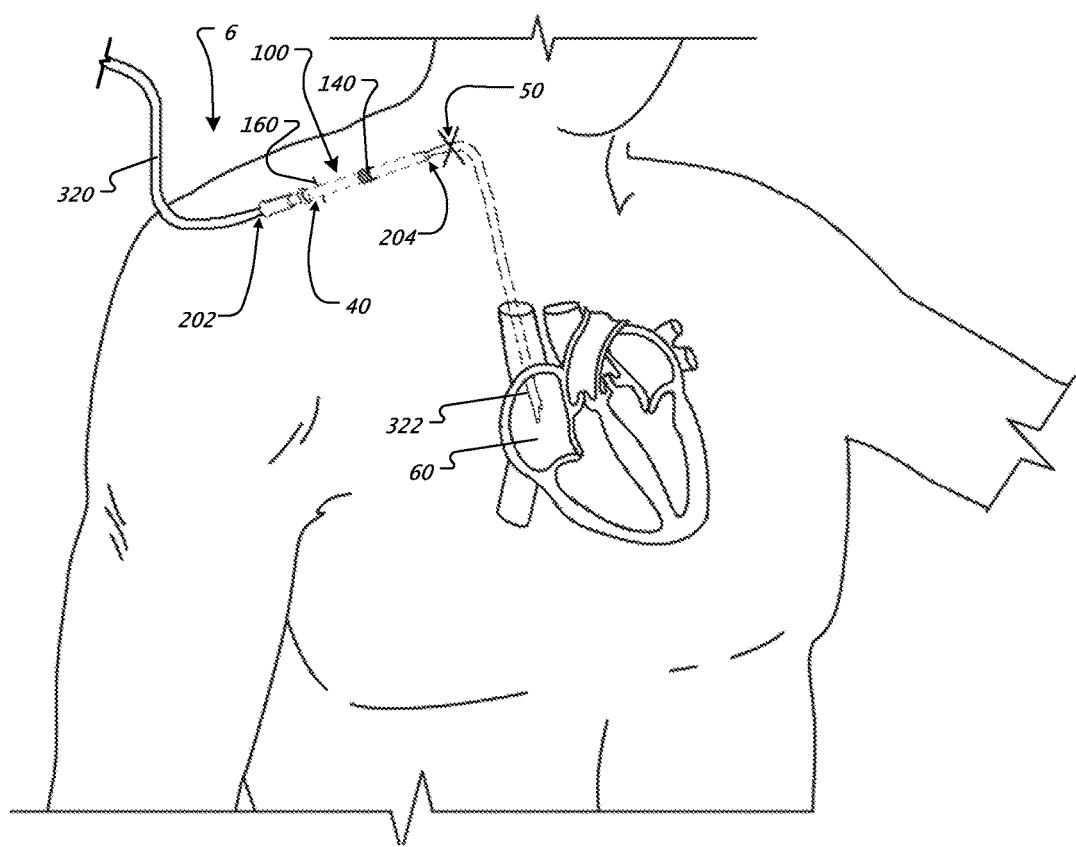
FIGS. 13-14 are perspective views of an anchor system used to advance a catheter device to a targeted site in a heart chamber.
Figure 14:
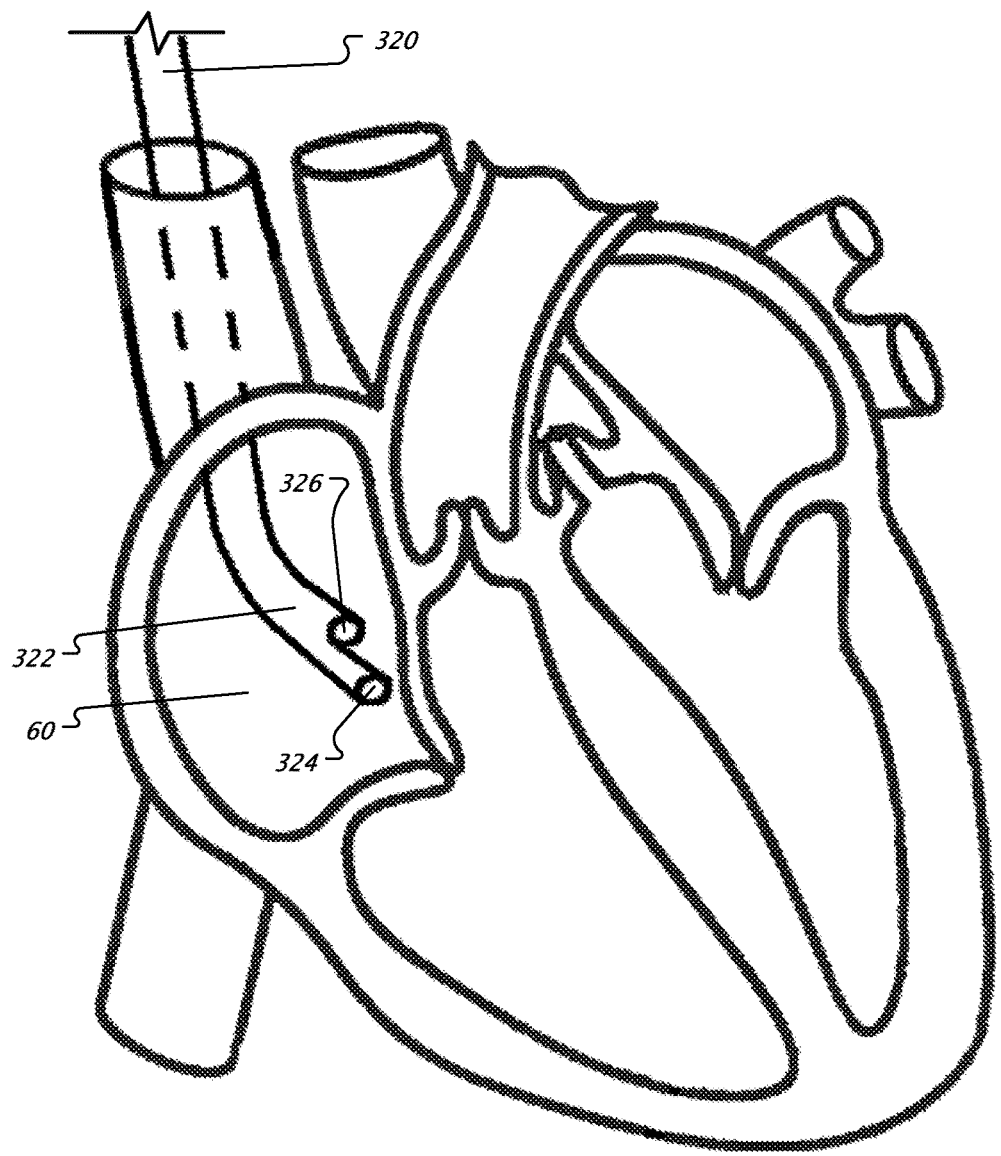

Referring now to FIGS. 13-14, particular embodiments of the sleeve device 100 may be particularly suited for use in providing chronic dialysis treatment. For example, the sleeve device 100 (shown here as the embodiment described in connection with FIGS. 1-8) can be used as part of a system 6 for the placement of a dialysis catheter 320, which may be used to provide long-term hemodialysis treatment. In some patients requiring long-term hemodialysis, a dialysis catheter tip 322 can be positioned in the superior vena cava or right atrium to provide the inlet and outlet of the extracorporeal circuit. As such, the cuff 140 of the sleeve device 100 can embed with the tissue in the subcutaneous region near the skin entry point so as to provide a barrier to infection. Because the path from the skin entry point (e.g., in the upper torso near the clavicle) to the targeted heart chamber 60 is not identical for all patient's, the system 6 advantageously permits the tip-to-cuff distance (e.g., the distance between the catheter tip 322 and the cuff 140) to be selectively adjusted by the practitioner during use.

In this example, a small incision 40 can be made in the upper torso (e.g., near the clavicle) through which the sleeve device 100 may be inserted and secured in the subcutaneous region as previously described. Similar to the embodiments described in connection with FIGS. 7-8, the sleeve device 100 may penetrate through the small incision and thereafter be advanced with the assistance of a dilation instrument. Once the sleeve device 100 has been inserted through the skin 10, at least a portion of the body 110 is located inside the subcutaneous region 20. In this example, the sleeve device 100 is inserted such that the distal tip portion 120, the cuff 140, and the anchor holes 112 are located inside the subcutaneous region 20 under the skin, and the actuator 170 and the stopper 180 remain external to the patient. The sleeve device 100 can be positioned such that the distal opening 204 is directed toward the jugular vein and the proximal opening 202 is external to the patient such that it can subsequently accept the catheter 320 or other medical instrument. Once the sleeve device 100 has been introduced, it can be anchored at least temporarily through the use of the deployed anchors 160. To deploy the anchors 160, the actuator 170 can be pulled back away from the stopper 180 (as previously described in connection with FIG. 8).

Still referring to FIG. 13, after the sleeve device 100 is at least temporarily secured in the subcutaneous region, the dialysis catheter 320 can be introduced through the working channel 200 (FIG. 8) of the sleeve device 100 and then directed toward the targeted heart chamber 60. In one example, the sleeve device 100 can inserted into the subcutaneous layer through a skin insertion point in the chest near the clavicle. The dialysis catheter 320 can be advanced through the working channel 200 of the sleeve and into the subcutaneous region where it passes through a subcutaneous tunnel toward the jugular vein. An access needle (not shown in FIG. 13) can be used to create a venous entry 50 into the jugular vein approximately one to two centimeters above the clavicle. For instance, the Seldinger technique may be used to access the jugular vein followed by placement of a peel-away sheath. Thereafter, the tip portion 322 of the dialysis catheter 320 is advanced through the peel-away sheath at the venous entry point 50 and is directed into the targeted heart chamber 60 (e.g., the right atrium in this example) via the superior vena cava using, for example, ultrasound imaging or fluoroscopy guidance. The dialysis catheter 320 may include one or more markers along the catheter body to provide visualization using the medical imaging system. The peel-away sheath can be promptly removed and any skin opening in the neck (e.g., temporary skin opening for insertion of peel-away sheath) can be closed. The anchor sleeve device 100 can be secured in position on the patient's chest so as to provide long-term access for the dialysis catheter 320.

As previously described in connection with FIG. 8, the cuff 140 of the sleeve device 100 can embed with the surrounding tissue in the subcutaneous region so as to serve as a barrier to infection and to serve as a long-term anchor of the sleeve device 100. The anchors 160 can be deployed for a period of time so as to retain the sleeve device 100 in place while the cuff 140 receives the tissue ingrowth. When the cuff 140 is embedded with the tissue, the anchors 160 can be transitioned to the non-deployed position inside the body 110 by pushing the actuator 170 in the direction of the stopper 180. Alternatively, the anchors 160 can be left in their deployed position in the subcutaneous layer 20 for the purpose of functioning as a supplemental anchoring feature.

Still referring to FIG. 13, catheter tip 322 can be advanced toward the targeted heart chamber 60 while the sleeve device 100 and cuff 140 remain generally stationary relative to the skin entry point. Accordingly, the distance between the cuff 140 and the catheter tip 322 (e.g., the tip-to-cuff distance) can be selectively adjusted depending on the patient's size, the patient's anatomy, the intended medical treatment, and other factors. As previously described, the tip-to-cuff distance can be advantageously selected by the practitioner while the catheter tip 322 is advanced through the patient's body. Also, the tip-to-cuff distance is adjustable at the time of insertion, so this distance need not be determined prior to the start of the procedure. Furthermore, this system 6 having the adjustable tip-to-cuff distance can reduce the need for hospitals or clinics to inventory a wide assortment of cuff-attached catheters, each having a non-adjustable tip-to-cuff length.

Referring now to FIG. 14, the dual lumen tip 322 of the dialysis catheter 320 can be arranged the right atrium 60 of the heart. After the final position of the tip 322 is verified using a medical imaging system, the dialysis catheter 320 can be used to perform the dialysis treatment. For example, the dialysis catheter 320 may include dual lumens that extend to distal ports at the staggered tip 322. In one embodiment, the staggered ports at the tip 322 may be separated by a distance of approximately one or two centimeters. The staggered position of these ports may facilitate the dialysis procedure. For example, a first port in the catheter tip 322 may be used to suction blood from the heart chamber 60 and into the extracorporeal circuit (not shown in FIGS. 13-14), and a second opening in the catheter tip 322 can be used to return the blood into the heart chamber. It should be understood that, in some embodiments, the sleeve device 100, 400, 410, or 420 described herein can be used with other medical instruments and can be used for treatments other than dialysis. For example, the sleeve device 100, 400, 410, or 420 can be used in combination with one or more Hickman catheters for delivery of chemotherapy treatment. The Hickman catheters may comprise single-lumen, double-lumen, or triple-lumen elongate bodies than can pass through one or more working channels of the sleeve device 100, 400, 410, or 420. In another example, the sleeve device 100, 400, 410, or 420 can be used in combination with at least one tunnel chest tube that is used to drain fluids from the lung cavity of the patient. In such circumstances, the sleeve device 100, 400, 410, or 420 can be retained in the subcutaneous region while the tunnel chest tube penetrates into the lung cavity (e.g., not necessarily into an artery or vein or the patient).

A number of embodiments of the invention have been described. Nevertheless, it will be understood that various modifications may be made without departing from the spirit and scope of the invention. Accordingly, other embodiments are within the scope of the following claims.

What is claimed is:

1. A catheter anchor device for securing a position of a catheter relative to a percutaneous opening in a skin layer occupied by the catheter, comprising:
    a proximal end, a distal end, and a length extending therebetween;
    a catheter engagement body configured to releasably secure with a catheter when the catheter is inserted into a percutaneous opening in a skin layer and extends distally away from the distal end;
    a subcutaneous anchor mechanism coupled to the catheter engagement body, the subcutaneous anchor mechanism having first and second flexible anchors that are adjustable to a deployed position in which the first and second flexible anchors are configured to abut an underside of the skin layer in a subcutaneous region; and
    a subcutaneous cuff device coupled to the catheter engagement body, the subcutaneous cuff device comprising a biocompatible material to receive ingrowth of bodily tissue when disposed in the subcutaneous region, wherein the subcutaneous cuff device is positioned closer to the distal end of the catheter anchor device than to the proximal end of the catheter anchor device, and wherein when the catheter is moved through the percutaneous opening in the skin layer, a cuff-to-tip distance between the subcutaneous cuff device and a distal tip of the catheter is manually selectable; and
    an actuator adjustable relative to the subcutaneous cuff device between a first position and a second position to simultaneously shift i) the catheter engagement body to secure the catheter in a fixed position relative to the subcutaneous cuff and ii) the flexible anchors to the deployed configuration.

2. The device of claim 1, wherein the subcutaneous cuff device is coupled to the catheter engagement body at a position such that the subcutaneous cuff device is configured to reside in the subcutaneous region along the underside of the skin layer while at least a proximal portion of the catheter engagement body resides external to the skin layer.

3. The device of claim 1, wherein the first and second flexible anchors are adjustable from a non-deployed orientation to a deployed orientation in the subcutaneous region along the underside of the skin layer.

4. The device of claim 1, wherein the catheter engagement body comprises a sleeve body.

5. The device of claim 4, wherein the sleeve body comprises a lumen configured to receive the catheter.

6. The device of claim 1, wherein at least a portion of the catheter engagement body is configured to adjust from a first position to a second position so as to simultaneously shift the flexible anchors to the second position and a gripper portion of the catheter engagement body to compress the outer surface of the catheter.

7. The device of claim 1, wherein the subcutaneous cuff device inhibits migration of infection when the cuff device is embedded in the subcutaneous region along the underside of the skin layer.

8. The device of claim 7, wherein the subcutaneous cuff device is configured to receive the ingrowth of bodily tissue over a period of time so as to inhibit the migration of infection from outside the skin and into the blood stream.

9. The device of claim 1, wherein the catheter engagement body includes a gripper portion that is adjustable to frictionally engage at least a portion of an outer circumferential surface of the catheter.

10. The device of claim 9, wherein the catheter engagement body is configured to releasably secure to the catheter by shifting the gripper portion to releasably compress against said portion of the outer circumferential surface of the catheter after each of the catheter and the flexible anchors is inserted through the percutaneous opening in the skin layer.

11. A catheter anchor device for securing a position of a catheter relative to a percutaneous opening in a skin layer occupied by the catheter, comprising:
    a subcutaneous cuff device;
    means for subcutaneously anchoring the catheter anchor device at a percutaneous opening in a skin layer so that the subcutaneous anchor means and the subcutaneous cuff device of the catheter anchor device are disposed in a subcutaneous region along an underside of the skin layer;
    means for receiving a catheter such that a distal tip of the catheter is movable relative to the subcutaneous cuff device to provide a distal length of the catheter extending distally from a distal end of the catheter anchor device that is greater than a maximum length of the catheter anchor, wherein the distance from the subcutaneous cuff device to the distal catheter tip defines a cuff-to-tip distance that is adjustable when the subcutaneous cuff device is disposed in the subcutaneous region along the underside of the skin layer; and
    means for simultaneously i) releasably securing the catheter to the catheter anchor device after the adjustment of the cuff-to-tip distance and ii) shifting the means for subcutaneously anchoring the catheter anchor device to a deployed configuration.

12. The device of claim 11, wherein the distal end of the catheter anchor device is configured to reside external to a venous entry point of a blood vessel that is occupied by the catheter after the distal tip of the catheter is advanced to the targeted body site.

13. The device of claim 11, wherein the subcutaneous cuff device comprises a biocompatible material that is configure to receive tissue ingrowth when disposed in the subcutaneous region along the underside of the skin layer.

14. The device of claim 11, wherein the means for subcutaneously anchoring comprises one or more flexible anchors configured to deploy in the subcutaneous region.

15. The device of claim 14, wherein the one or more flexible anchors are adjustable from a non-deployed orientation to a deployed orientation in the subcutaneous region along the underside of the skin layer.

16. The device of claim 11, wherein the means for receiving the catheter comprises at least a lumen of a sleeve body.

17. The device of claim 16, wherein the subcutaneous cuff device is positioned closer to the distal end of the sleeve body than to the proximal end of the sleeve body.

18. The device of claim 11, wherein the subcutaneous cuff device is configured to inhibit migration of infection when the cuff device is embedded in the subcutaneous region along the underside of the skin layer.

19. The device of claim 18, wherein the subcutaneous cuff device is configured to receive the ingrowth of bodily tissue over a period of time so as to inhibit the migration of infection from outside the skin and into the blood stream.

* * * * *